United States Patent [19]
Marosi et al.

[11] 4,456,582
[45] Jun. 26, 1984

[54] MANUFACTURE OF NITROGEN-CONTAINING CRYSTALLINE METAL SILICATES HAVING A ZEOLITE STRUCTURE

[75] Inventors: Laszlo Marosi, Ludwigshafen; Joachim Stabenow, Weinheim; Matthias Schwarzmann, Limburgerhof, all of Fed. Rep. of Germany

[73] Assignee: BASF Aktiengesellschaft, Fed. Rep. of Germany

[21] Appl. No.: 45,175

[22] Filed: Jun. 4, 1979

[30] Foreign Application Priority Data

Jul. 13, 1978 [DE] Fed. Rep. of Germany ....... 2830787

[51] Int. Cl.$^3$ ...................... C01B 33/28; C01B 33/20; C01B 35/10
[52] U.S. Cl. .................................. 423/277; 423/326; 423/328; 423/329; 260/448 C; 502/74; 502/77; 502/202; 502/64
[58] Field of Search ............................... 423/326–330, 423/276, 277; 260/448 C; 252/431 N, 455 Z

[56] References Cited

U.S. PATENT DOCUMENTS

| 4,108,881 | 8/1978 | Rollmann et al. | 423/328 X |
| 4,139,600 | 2/1979 | Rollmann et al. | 423/328 X |
| 4,151,189 | 4/1979 | Rubin et al. | 423/329 X |
| 4,285,919 | 8/1981 | Klotz et al. | 423/277 |

FOREIGN PATENT DOCUMENTS 984502 2/1965 United Kingdom ................ 423/328

Primary Examiner—Edward J. Meros
Assistant Examiner—Jackson Leeds
Attorney, Agent, or Firm—Keil & Weinkauf

[57] ABSTRACT

A process for the manufacture of a nitrogen-containing crystalline metal silicate having a zeolite structure from silicon dioxide and a metal oxide and/or metal hydroxide, wherein the crystallization is carried out in the absence of an alkali metal in an aqueous solution of hexamethylenediamine, preferably under the autogeneous pressure of the solution at from 100° to 200° C. The zeolites are preferably used as catalysts for the reaction of methanol and/or dimethyl ether to give unsaturated hydrocarbons, the oligomerization of olefins, the alkylation of aromatics, and other conversions of hydrocarbons.

8 Claims, No Drawings

MANUFACTURE OF NITROGEN-CONTAINING CRYSTALLINE METAL SILICATES HAVING A ZEOLITE STRUCTURE

The present invention relates to a process for the manufacture of nitrogen-containing crystalline metal silicates having a zeolite structure, the novel metal silicates manufactured by this process, and their use as catalysts.

The commonest zeolites of the A, X and Y type have acquired great industrial importance. They are employed industrially as ion exchangers, molecular sieves and catalysts. Industrial processes such as catalytic cracking and hydro-cracking of hydrocarbons are carried out with zeolite catalysts. Recently, zeolites of the ZMS-5 or ZMS-8 type have increasingly become of interest for catalyzing novel reactions, for example the conversion of methanol into liquid hydrocarbons. However, the conventional zeolite catalysts of this type suffer from certain disadvantages which detract from their usefulness for the above processes. The principal disadvantage is the expense entailed in the manufacture of these zeolites. They are manufactured in the presence of sodium, using quaternary organic nitrogen bases or organic amines, eg. n-propylamine. Furthermore, the alkali metal-containing zeolites initially obtained from the synthesis process cannot be employed directly as catalysts. Instead, they must be converted to an acidic H-form free from alkali metal. This conversion as a rule comprises a multi-stage ion exchange which frequently also entails several intermediate calcination treatments. In the ion exchange process, the alkali metal cations are replaced by ammonium ions and the catalytically active hydrogen-form is produced from the ammonium ion form by thermal decomposition. The repeated ion exchange with $NH_4$ salts, which in industrial practice is carried out with a large excess of the ammonium salt, furthermore creates environmental problems. It is therefore desirable to be able to manufacture the zeolites directly in the catalytically active form, free from alkali metal, in order to overcome the above disadvantages.

However, it has hitherto not proved possible to synthesize catalytically active zeolites free from alkali metal cations or alkaline earth metal cations. The literature discloses only a single type of zeolite which can be synthesized free from alkali metal (Helv. Chim. Acta 53 (1970), 1,285). However, this Na-free gismodite is totally unimportant as a catalyst.

With all other types of zeolite which have been manufactured in the presence of organic nitrogen-containing cations, attention is expressly drawn to the need to have alkali metal cations present during the synthesis, and furthermore the zeolite produced contains significant amounts of alkali metal ions which must be removed from the zeolite by ion exchange.

By way of example, the synthetic crystalline nitrogen-containing molecular sieves of the A, X and Y type cannot be synthesized without Na ions, and furthermore the zeolite produced has a high Na content. In the case of the synthetic crystalline nitrogen-containing molecular sieves ZMS-5 and ZMS-8, the synthesis mixture must contain an amount of Na at least equivalent to the aluminum employed, and the zeolite produced also has a high Na content.

It is a feature of all the zeolite types mentioned above that whilst they have a substantially identical crystal lattice structure, they nevertheless are individual materials in their own right. For example, zeolites ZMS-5 and ZMS-8 differ in their cation balance, in such a way that they cannot be inter-converted by ion exchange. Furthermore, the nitrogen-containing molecular sieves of the A type also differ from one another by the Si/Al ratio in their crystal lattice, and by their different catalytic activity.

A further common feature of the zeolite types hitherto disclosed is that they are virtually exclusively crystalline aluminosilicates. Their composition is derived from a polysilicate $[SiO_{4/2}]\infty$. If some of the Si atoms are replaced by Al atoms, the missing valency electrons are supplied by the incorporation of cations. According to the prior art, at least some of these cations must be alkali metal ions or alkaline earth metal ions. Lattice substitutions, ie. the isomorphous replacement of Al and/or Si by other elements, at the present time offers only very limited scope for producing zeolites having novel properties.

It is an object of the present invention to synthesize, from cheap starting materials, novel catalytically active zeolites which are formed in a Na-free form and can therefore be employed directly, without prior ion exchange, and at most after a simple calcination, as a catalyst.

We have found that this object is achieved and that novel nitrogen-containing crystalline metal silicates having a zeolite structure and conforming to the above conditions are obtained from mixtures of silicon dioxide and metal oxides and/or metal hydroxides if the crystallization is carried out in the absence of an alkali metal, in an aqueous hexamethylenediamine solution.

It is surprising that a whole series of novel metal silicate zeolites can be prepared under the crystallization conditions according to the invention, including zeolites which no longer contain any aluminum. In place of aluminum, various trivalent metals may be employed, for example boron, arsenic, antimony, vanadium, iron or chromium. In the case of the aluminum, boron and iron silicate zeolites, it has been possible to demonstrate that these elements are predominantly incorporated at tetrahedral lattice positions of the crystal lattice. The elements chromium, vanadium and arsenic are probably only partially built into the crystal lattice whilst partially they are accommodated in the intracrystalline pores and possess no defined lattice positions. The present invention provides the possibility of imparting the unique properties of zeolite aluminosilicates also to other metal silicates and thereby substantially extending the possible applications of zeolites.

In a preferred embodiment of the synthesis of the novel Na-free nitrogen-containing zeolites, a reaction mixture of $SiO_2$ and metal oxide or metal hydroxide or its sodium-free intermediate is heated in an aqueous hexamethylenediamine solution for from 1 to 8 days at from 100° to 200° C., preferably from 2 to 4 days at from 140° to 160° C., under autogenous pressure. The novel compounds have a zeolite structure resembling those of zeolites ZMS-5 and ZMS-8, but differ from these especially in respect of their composition. They contain, according to the invention, no alkali metal, and are furthermore synthesized in the absence of alkali metal ions. Free from alkali metal, for the purposes of the invention, means essentially free from sodium ions. The residual alkali metal content of such zeolites is in principle only attributable to impurities of the chemicals used as starting materials. It is known that industrial chemicals always contain traces of sodium. Thus, commercial pyrogenic silica (Aerosil), which is a particularly suitable starting material, contains about 4 ppm of $Na_2O$. The reactive metal oxides or hydroxides required for the process of preparation also frequently have an undesirable Na content. It is possible that traces of Na may accelerate the crystallization. However, it is expressly pointed out that in the manufacture of the zeolites according to the invention chemicals of low Na content are fundamentally preferred, so that substantially Na-free zeolites are produced which can, without subsequent ion exchange, be employed as catalysts. it is true that any Na ions present have no adverse effect on the synthesis process, but they do, under certain circumstances, necessitate a subsequent expensive cation exchange process. In addition to this essential difference of the absence of alkali metal and, in some cases, absence of aluminum, the cations which compensate the negative charges of the $[MeO_{4/2}]^-$ tetrahedra differ according to the amine and cannot be interconverted at will by ion exchange.

The zeolites manufactured according to the invention may for example be used for cracking and hydro-cracking processes, but also for isomerization reactions and alkylation reactions. They are manufactured by reacting a mixture, which contains an aqueous amine solution, a metal oxide and/or hydroxide or its alkali metal-free intermediate, and silica at from 100° to 200° C. Particularly suitable starting materials for the manufacture of the zeolites are metal nitrates, metal sulfates, metal oxides, metal hydroxides and hydrated metal oxides, but also other compounds which furnish the reactive metal oxide. The source of $SiO_2$ is advantageously pyrogenic silica (Aerosil) or an $SiO_2$ sol, but other reactive types of $SiO_2$ can also be employed. Furthermore, reactive metal silicate gels, which can be prepared, for example, by precipitation from waterglass and a metal salt, and washing the precipitate free from alkali metal, can also be used. The concentration of the hexamethylenediamine solution can be from 5 to 90%, advantageously from 20 to 75%. A 50% strength solution is particularly suitable. The starting materials for the metal oxides and $SiO_2$ are introduced into the hexamethylenediamine solution and homogenized therein by stirring. The homogeneous gel is then heated in an autoclave under autogenous pressure until a crystalline product has formed, which requires, for example, from 2 to 5 days at 150° C.

The metal silicate zeolites thus produced as a rule contain major amounts of the hexamethylenediamine used accommodated in the intra-crystalline pores. The amine can be removed from the pores by, for example, combustion, whereby catalytically active materials are produced.

A great advantage of the process according to the invention is that, for example when using metal oxides or metal hydroxides, the mother liquor can be fully reused for the manufacture of fresh zeolite. This is achieved in particular by the process of manufacture being carried out in the absence of Na.

The Examples which follow illustrate the process according to the invention.

The diffraction diagram data given in Tables 1 to 4 were obtained with an automatic Phillips diffractometer APD-10. Copper radiation and a graphite monochromator were used.

Analytical data quoted are based on dry material. Before chemical analysis, the substances were calcined at 550° C. until the amines contained therein had been combusted. The difference from 100% is accounted for by small amounts of adsorbed water.

EXAMPLE 1

160 g of Aerosil and freshly precipitated $Al(OH)_3$ (the latter being prepared from 61.4 g of $Al(NO_3)_3.9-H_2O$ by precipitation with ammonia) are introduced into 2,000 g of 25% strength hexamethylenediamine solution at 60° C. The $SiO_2/Al_2O_3$ molar ratio in the mixture is 32.6. The mixture is stirred until it is homogeneous and is then heated for 5 days at 150° C. under autogenous pressure in a steel autoclave. The crystalline product is filtered off, washed and dried at 100° C. According to X-ray analysis, it consists of well-crystallized aluminum zeolite. Chemical analysis indicates a Na content of 0.004% by weight. Analysis of the mother liquor gives the following values: 0.5 ppm of $Na_2O$, 0.02 ppm of $SiO_2$ and 1 ppm of $Al_2O_3$. The yield of aluminum zeolite, based on $Al_2O_3$ and $SiO_2$ employed, is virtually quantitative.

EXAMPLE 2

In contrast to Example 1, the same amount by weight of a 50% strength hexamethylenediamine solution or 70% strength hexamethylenediamine solution is used. The remaining reaction conditions are unchanged. These experiments also give well-crystallized aluminum zeolite.

EXAMPLE 3

Two experiments are carried out, each with 2,000 g of a 50% strength hexamethylenediamine solution. The amounts of the other reactants are as in Example 1. The reaction time is, respectively, 2.5 and 3 days at 150° C. The reaction product is crystalline in both cases and after calcination at 550° C. exhibits an X-ray diffraction diagram characteristic of the aluminum zeolite and having the following significant d-values:

TABLE 1

| Interplanar spacing d (Å) | Relative intensity $(I/I_o)$ |
| --- | --- |
| 11.02 | 83 |
| 9.90 | 64 |
| 5.94 | 18 |
| 5.54 | 13 |
| 4.98 | 8 |
| 4.35 | 7 |
| 3.83 | 100 |
| 3.70 | 43 |
| 3.62 | 21 |
| 3.32 | 9 |
| 3.30 | 7 |
| 3.04 | 10 |
| 2.97 | 11 |
| 2.60 | 5 |
| 2.48 | 5 |
| 2.39 | 4 |
| 2.00 | 10 |
| 1.98 | 9 |

EXAMPLE 4

In this experiment, 1,650 g of mother liquor, isolated from experiments with 50% strength hexamethylenediamine solution, are employed instead of the original hexamethylenediamine solution. The reaction time is 4 days and the remaining parameters correspond to those in Example 1. Again, a well-crystallized aluminum zeolite is obtained. The mother liquor contains 0.5 ppm of Na$_2$O, and the Aerosil employed contains about 4 ppm of Na$_2$O.

EXAMPLE 5

160 g of Aerosil and freshly precipitated Al(OH)$_3$ (prepared from 30.7 g of Al(NO$_3$)$_3$.9H$_2$O by precipitation with ammonia) are introduced into 2,000 g of 50% strength hexamethylenediamine solution. The SiO$_2$/Al$_2$O$_3$ molar ratio in the mixture is about 100. The mixture is stirred until it is homogeneous and is subsequently heated for 5 days at 150° C. under autogenous pressure in a steel autoclave. The crystalline product is filtered off, washed and dried at 100° C. According to X-ray analysis, it consists of a well-crystallized aluminum zeolite. The product obtained is calcined for 10 hours at 550° C. and then analyzed. The chemical analysis gives the following results: 0.002% of Na$_2$O, 1.53% of Al$_2$O$_3$, 96.3% of SiO$_2$.

EXAMPLE 6

In contrast to the preceding Examples, 110 g of Al$_2$(SO$_4$)$_3$.18H$_2$O are employed in place of aluminum hydroxide. 160 g of Aerosil are stirred into 2,000 g of 50% strength hexamethylenediamine solution and a saturated aqueous solution of 110 g of Al$_2$(SO$_4$)$_3$.18H$_2$O is then added. The resulting mixture is heated for 4 days at 160° C. and the product is then filtered off and washed. This product again consists of well-crystallized aluminum zeolite.

EXAMPLE 7

This Example describes the preparation of a crystalline Na-free borosilicate. 160 g of Aerosil are stirred into 1,700 g of 50% strength hexamethylenediamine solution and a solution of 10.1 g of boric acid in 300 g of 50% strength hexamethylenediamine solution is added to this suspension at 60° C. The resulting mixture is homogenized by stirring for about 15 minutes and is then heated for 5 days at 150° C. under autogenous pressure in a steel autoclave. The crystalline product is filtered off, washed and dried at 100° C. It consists of well-crystallized boron zeolite.

A portion of the crystals is calcined for about 10 hours at 550° C. Chemical analysis gives the following result: 0.0035% of Na$_O$, 0.73% of B$_2$O$_3$, 91.5% of SiO$_2$ molar ratio SiO$_2$/B$_2$O$_3$=145.

X-ray diffraction analysis gives the following significant d-values after calcination at 550° C.:

TABLE 2

| EXAMPLE 7 | | EXAMPLE 8 b | |
|---|---|---|---|
| Interplanar spacing d (Å) | Relative intensity (I/I$_o$) | Interplanar spacing d (Å) | Relative intensity (I/I$_o$) |
| 10.95 | 67 | 10.96 | 55 |
| 9.85 | 59 | 9.77 | 43 |
| 5.93 | 19 | 5.91 | 12 |
| 5.53 | 10 | 5.51 | 9 |
| 4.98 | 9 | 4.33 | 9 |
| 3.81 | 100 | 3.80 | 100 |
| 3.69 | 32 | 3.69 | 43 |
| 3.62 | 21 | 3.63 | 19 |
| 3.03 | 7 | 3.30 | 10 |
| 2.96 | 13 | 3.02 | 8 |
| 1.995 | 10 | 2.95 | 12 |
| 1.989 | 8 | 1.985 | 10 |
| | | 1.979 | 9 |

EXAMPLE 8

A 50% strength hexamethylenediamine solution is employed in 2 experiments. 2.5 g of boric acid are used in experiment (a) and 20.2 g in experiment (b). The remaining reaction conditions are maintained as in Example 7. In both cases, the reaction product is crystalline. Sample 8b exhibits an X-ray diffraction diagram with the d-values shown in Table 2, after calcination at 550° C.

EXAMPLE 9

This Example describes the preparation of a crystalline Na-free arsenic silicate.

11.45 g of Aerosil are stirred into 88 g of 50% strength hexamethylenediamine solution at 70° C. and a solution of 2.32 g of As$_2$O$_3$ in 30 g of 50% strength hexamethylenediamine solution is added to this suspension. The resulting mixture is heated for 5 days at 150° C. under autogenous pressure. The resulting product is filtered off, washed and dried at 100° C. It consists of well-crystallized arsenic zeolite.

Chemical analysis of the calcined product gives the following result: 0.008% of Na$_2$O, 0.25% of As$_2$O$_3$, 96.0% of SiO$_2$.

The result of the X-ray diffraction analysis is summarized in Table 3:

TABLE 3

| Interplanar spacing d (Å) | Relative intensity (I/I$_o$) |
|---|---|
| 11.12 | 52 |
| 9.99 | 73 |
| 9.97 | 6 |
| 6.70 | 5 |
| 6.36 | 6 |
| 5.97 | 21 |
| 5.69 | 6 |
| 5.56 | 9 |
| 5.01 | 9 |
| 4.60 | 3 |
| 3.846 | 100 |
| 3.818 | 62 |
| 3.744 | 17 |
| 3.712 | 21 |
| 3.620 | 20 |

EXAMPLE 10

This Example describes the preparation of a crystalline Na-free antimony silicate.

11.45 g of Aerosil are stirred into 88 g of 50% strength hexamethylenediamine solution at 60° C., and a suspension of 3.42 g of Sb$_2$O$_3$ in 30 g of 50% strength hexamethylenediamine solution is added to this mixture. The resulting homogeneous mixture is heated for 5 days at 150° C. under its autogenous pressure. The resulting product is filtered off, washed and dried at 100° C.

The diffraction diagram of the product shows, in addition to Sb$_2$O$_3$, a further crystalline component, the diffraction lines of which essentially correspond to the lines indicated in Table 1.

EXAMPLE 11

This Example shows that under the reaction conditions according to the invention mixtures of hexamethylenediamine, water and Aerosil, without addition of Al oxides, B oxides or As oxides or Sb oxides do not crystallize to give the crystalline compounds which have been described.

22.9 g of Aerosil are introduced into 236 g of 50% strength hexamethylenediamine solution and the mixture is homogenized by stirring. The resulting mixture is divided into two parts and heated for 5 days at 150° C. or 175° C. under autogenous pressure in a steel autoclave. The reaction products obtained are gel-like and their diffraction diagrams do not show any diffraction lines of the compounds described above.

EXAMPLE 12

100 g of the boron zeolite obtained in Example 7 are processed with boehmite to give pellets 1 mm in diameter, which are then calcined for 10 hours at 550° C. The zeolite content of the pellets is 65% by weight. 20 g of this catalyst are then introduced into a flow reactor and the activity of the catalyst in various reactions is tested:

(a) Olefin oligomerization

Propylene at a rate of 40 g/h is passed over the catalyst at 380° C. The conversion is about 50%. The liquid reaction product obtained has the following composition:

13% of aromatics
20% of aliphatics
67% of $C_5$–$C_9$-olefins (b) Conversion of methanol Crude methanol containing 17% by weight of water is dehydrated at 370° C. over an aluminum oxide catalyst and the resulting gas mixture is converted over the zeolite catalyst at 370° C. The throughput is 46 g of dimethyl ether/h. The reaction conditions are summarized in the Table which follows:

| | |
|---|---|
| input temperature: | 370° C. |
| pressure: | 1.14 bar |
| temperature rise: | 70° C. |
| conversion: | 95–100% |
| total throughput, g of dimethyl ether: | 120 g |

The reaction product obtained has the following composition:

25% by weight, based on $CH_2$ equivalent of the methanol employed, of an oil comprising 40% of aromatics, 13% of aliphatics and 47% of $C_5$–$C_9$-polyolefins.

Gaseous reaction products: 75% by weight, based on $CH_2$ employed, of a gaseous reaction product comprising 8.6% by weight of ethylene, 58% by weight of propylene, 17.5% by weight of butenes, 2.75% by weight of methane, 3.75% by weight of propane and 9% by weight of butanes.

EXAMPLE 13

100 g of the zeolite obtained in Example 2 are processed with boehmite to give pellets 1 mm in diameter, which are then calcined for 10 hours at 550° C. The zeolite content of the pellets is 65% by weight.

18 g of this catalyst are introduced into a flow reactor and (a) the activity in the conversion of methanol to olefins is tested.

The reaction conditions and the experimental results are shown in the Table which follows:

| | |
|---|---|
| input temperature | 370° C. |
| temperature rise | 100° C. |
| pressure | 1.2 bar |
| feed — $CH_3OH$ (g) | 62 |
|     — $H_2O$ (g) | 180 |
| throughput (feed/h) | 400 g |
| total throughput, g of methanol | 730 g |
| conversion | 95–100% |

A reaction product of the following composition is obtained:

| | | |
|---|---|---|
| oil | | 22 g |
| gaseous hydrocarbon (% by volume) | | |
| olefins | $C_2$ | 30 |
| | $C_3$ | 32 |
| | $C_4$ | 17 |
| paraffins | $C_1$ | 2 |
| | $C_2$ | traces |
| | $C_3$ | 3 |
| | $C_4$ | 13 |

(b) The activity of the catalyst in the alkylation of benzene with ethylene was tested.

| | |
|---|---|
| Reaction temperature: | 400° C. |
| pressure: | bar |
| throughput: | 6 g of ethylene/h |
| | 12 g of benzene/h |

Composition of the reaction products
17% by weight of ethylbenzene
1.5% by weight of diethylbenzene
0.1% by weight of toluene
81.5% by weight of benzene.

The reaction time is about 60 hours. The selectivity over this period is 98–100% and the ethylene conversion is >95%.

We claim:

1. A process for the manufacture of a nitrogen-containing crystalline metal silicate having a zeolite structure which comprises:

adding a metal oxide, metal hydroxide, metal sulfate, metal nitrate or hydrated metal oxide and a silicon dioxide source that is essentially free of alkali metal to a 5 to 90% strength aqueous solution of hexamethylenediamine to form a mixture that is essentially free of alkali metal;

stirring the mixture to form a homogeneous gel; and thereafter heating the gel to form the crystalline metal silicate; wherein said metal is selected from the group consisting of aluminum, boron, arsenic, antimony, vanadium, iron and chromium, and whereby said crystalline metal silicate is essentially free of alkali metal.

2. A process as set forth in claim 1, wherein the crystallization is carried out under the atuogenous pressure of the solution, at from 100° to 200° C.

3. A process as set forth in claim 1, wherein a hexamethylenediamine solution of from 20 to 75% strength is used.

4. A process as set forth in claims 1, 2 or 3, wherein the crystalline metal silicate having a zeolite structure is calcined to remove hexamethylenediamine from the pores of the silicate.

5. A process as set forth in claims 1, 2, or 3, wherein the metal is aluminum.

6. A process as set forth in claims 1, 2, or 3, wherein the metal is boron.

7. A process as set forth in claims 1, 2 or 3, wherein pyrogenic silica is used as the source of silicon dioxide.

8. A process as set forth in claims 1, 2 or 3, wherein the source of silicon dioxide is a silica gel prepared by precipitating waterglass and washing the precipitate free of sodium.